United States Patent [19]

Rosen et al.

[11] Patent Number: 5,328,931
[45] Date of Patent: Jul. 12, 1994

[54] N-ALKYLATED 1,4-DIHYDROPYRIDINEDICARBOXYLIC ACID ESTERS

[75] Inventors: Bruno Rosen, Wülfrath; Siegfried Zaiss; Hartmund Wollweber, both of Wuppertal; Maarten de Jonge, Overath-Steinenbrück; Hans-Georg Dellweg, Wuppertal, all of Fed. Rep. of Germany

[73] Assignee: Bayer Aktiengesellschaft, Leverkusen, Fed. Rep. of Germany

[21] Appl. No.: 917,565

[22] Filed: Jul. 21, 1992

[30] Foreign Application Priority Data

Jul. 31, 1991 [DE] Fed. Rep. of Germany ....... 4125271

[51] Int. Cl.$^5$ ................. C07D 213/55; A61K 31/455
[52] U.S. Cl. ..................................... 514/356; 546/322
[58] Field of Search ........................ 546/322; 514/356

[56] References Cited

U.S. PATENT DOCUMENTS

| | | | |
|---|---|---|---|
| 3,883,540 | 5/1975 | Meyer et al. | 546/321 |
| 4,044,141 | 8/1977 | Bossert et al. | 546/322 |
| 4,284,634 | 8/1981 | Satu | 546/322 |

FOREIGN PATENT DOCUMENTS

| | | | |
|---|---|---|---|
| 240828 | of 0000 | European Pat. Off. | 546/322 |
| 0322747 | 7/1989 | European Pat. Off. | 546/322 |
| 0451654 | 3/1991 | European Pat. Off. | 546/322 |
| 1923990 | 11/1970 | Fed. Rep. of Germany | 546/322 |
| 1963188 | 6/1971 | Fed. Rep. of Germany | 546/322 |
| 2210667 | 9/1973 | Fed. Rep. of Germany | 546/322 |

OTHER PUBLICATIONS

T. D. Harris et al., J. Org. Chem. 44 (1979) 2004.
W. J. Dale et al., J. Am. Chem. Soc. 78 (1956) 2543.
CA 59 13929 (1963).
Chemical Abstract, vol. 110, No. 11 Mar. 13, 1989, Columbus, Ohio, USA; Abstract No. 95014J "Preparation of Optically Active Dihydropridine Carboxylic Acid Esters as Cardiovascular Agents", p. 686.
Chemical Abstracts, vol. 114, No. 25, Jun. 24, 1991, Columbus, Ohio, US: abstract No. 247146B, "Preparation of Phenyldihydropyridine Derivatives as Calcium Antagonists and Antihypertensives", p. 748.
Trends Pharmacol. Sci. vol. 11, No. 8, 1990, pp. 309–310; "Nimodipine and the Recovery of Memory".
Physiol. Behav. vol. 42, No. 5, 1988, pp. 447–452; "The Effect of a calcium Antagonist on the Retention of Simple Associational Learning".

Primary Examiner—C. Warren Ivy
Assistant Examiner—Zinna N. Davis
Attorney, Agent, or Firm—Sprung Horn Kramer & Woods

[57] ABSTRACT

N-alkylated 1,4-dihydropyridinedicarboxylic acid esters can be prepared either by reaction of aldehydes with acetoacetic esters and amines, optionally with isolation of the corresponding ylidene compounds, or by reaction of aminocrotonic acid esters with ylidene compounds and subsequent alkylation of the NH function. The N-alkylated 1,4-dihydropyridinedicarboxylic acid esters can be employed as active compounds in medicaments, in particular as cerebral therapeutics.

11 Claims, No Drawings

N-ALKYLATED 1,4-DIHYDROPYRIDINEDICARBOXYLIC ACID ESTERS

The invention relates to novel N-alkylated 1,4-dihydropyridinedicarboxylic acid esters, processes for their preparation and their use in medicaments, in particular as cerebral therapeutics in disturbances of neuronal function.

It has already been disclosed that 1,4-dihydropyridinedicarboxylic acid esters have a calcium antagonistic or calcium agonistic action and can thus be employed as circulation-influencing agents [compare, for example, German Offenlegungsschrift 2,506,987; German Offenlegungsschrift 2,210,667; EP 240,828].

The present invention relates to N-alkylated 1,4-dihydropyridinedicarboxylic acid esters of the general formula (I)

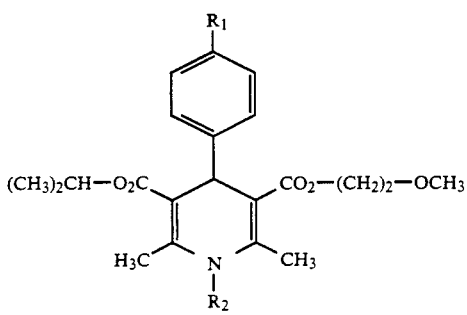

in which
R$^1$ represents trifluoromethoxy, cyano, fluorine, chlorine or trifluoromethyl,
R$^2$ represents methyl, ethyl or cyclopropyl, with the proviso that R$^1$ must not represent trifluoromethyl if R$^2$ denotes methyl.

The compounds according to the invention can exist in stereoisomeric forms, which either behave as image and mirror image (enantiomers), or which do not behave as image and mirror image (diastereomers). The invention relates both to the antipodes and to the racemic modifications. The racemic modifications can be separated in a known manner into the stereoisomerically uniform components [compare E. L. Eliel, Stereochemistry of Carbon Compounds, McGraw Hill, 1962].

The following compounds of the general formula (I) are preferred:
isopropyl 2-methoxyethyl 1,2,6-trimethyl-4-(4-trifluoromethoxyphenyl)-1,4-dihydropyridine-3,5-dicarboxylate, isopropyl 2-methoxyethyl 1,2,6-trimethyl-4-(4-cyanophenyl)-1,4-dihydropyridine-3,5-dicarboxylate, isopropyl 2-methoxyethyl 1-ethyl-2,6-dimethyl-4-(4-trifluoromethoxyphenyl)-1,4-dihydropyridine-3,5-dicarboxylate,
isopropyl 2-methoxyethyl 1,2,6-trimethyl-4-(4-chlorophenyl)-1,4-dihydropyridine-3,5-dicarboxylate, isopropyl 2-methoxyethyl 1,2,6-trimethyl-4-(4-fluorophenyl)-1,4-dihydropyridine-3,5-dicarboxylate, isopropyl 2-methoxyethyl 1-ethyl-2,6-dimethyl-4-(4-trifluoromethylphenyl)-1,4-dihydropyridine-3,5-dicarboxylate,
isopropyl 2-methoxyethyl 1-cyclopropyl-2,6-dimethyl-4-(4-trifluoromethoxyphenyl)-1,4-dihydropyridine-3,5-dicarboxylate, in the form of their racemates, (+)- or (−)-isomers.

The following compounds of the general formula (I) are particularly preferred:
isopropyl 2-methoxyethyl (±)-1,2,6-trimethyl-4-(4-trifluoromethoxyphenyl)-1,4-dihydropyridine-3,5-dicarboxylate,
isopropyl 2-methoxyethyl (+)-1,2,6-trimethyl-4-(4-trifluoromethoxyphenyl)-1,4-dihydropyridine-3,5-dicarboxylate,
isopropyl 2-methoxyethyl (−)-1,2,6-trimethyl-4-(4-trifluoromethoxyphenyl)-1,4-dihydropyridine-3,5-dicarboxylate,
isopropyl 2-methoxyethyl(±)-1,2,6-trimethyl-4-(4-chlorophenyl)-1,4-dihydropyridine-3,5-dicarboxylate,
isopropyl 2-methoxyethyl(+)-1,2,6-trimethyl-4-(4-chlorophenyl)-1,4-dihydropyridine-3,5-dicarboxylate,
isopropyl 2-methoxyethyl(−)-1,2,6-trimethyl-4-(4-chlorophenyl)-1,4-dihydropyridine-3,5-dicarboxylate.

The following compounds of the general formula (I) are very particularly preferred:
isopropyl 2-methoxyethyl (±)-1,2,6-trimethyl-4-(4-trifluoromethoxyphenyl)-1,4-dihydropyridine-3,5-dicarboxylate,
isopropyl 2-methoxyethyl (+)-1,2,6-trimethyl-4-(4-trifluoromethoxyphenyl)-1,4-dihydropyridine-3,5-dicarboxylate,
isopropyl 2-methoxyethyl (−)-1,2,6-trimethyl-4-(4-trifluoromethoxyphenyl)-1,4-dihydropyridine-3,5-dicarboxylate.

The compounds of the general formula (I) according to the invention can be prepared by
[A] converting aldehydes of the general formula (II)

in which
R$^1$ has the abovementioned meaning,
first either with isopropyl acetoacetate of the formula (III) or with 2-methoxyethyl acetoacetate of the formula (IV)

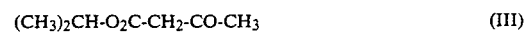

optionally with isolation, into the corresponding ylidene compounds of the general formula (V) or (VI)

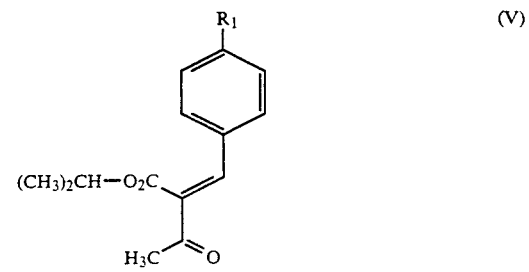

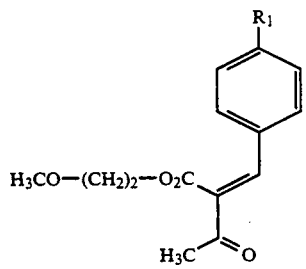

in which
R¹ has the abovementioned meaning,
then in the case of the compounds of the general formula (V) reacting these with 2-methoxyethyl acetoacetate of the formula (IV) and in the case of the compounds of the general formula (VI) reacting these with isopropyl acetoacetate of the formula (III)
and with amines or the corresponding amine hydrochlorides of the general formula (VII)

$$H_2N\text{-}R^2 \qquad (VII)$$

in which
R² has the abovementioned meaning,
in inert solvents or
[B] in the case in which R² represents methyl or ethyl, first reacting the compounds of the general formula (V) with 2-methoxyethyl aminocrotonate of the formula (VIII)

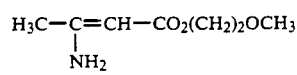

or first reacting the compounds of the general formula (VI) with 2-isopropyl β-aminocrotonate of the formula (IX)

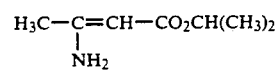

in inert solvents and in a last step alkylating the —NH function by a customary method, if appropriate in the presence of a base
and in the case of the enantiomerically pure esters, either performing a direct chromatographic separation or optionally preparing the respective enantiomerically pure carboxylic acids and esterifying these by a customary method, if appropriate via a reactive acid derivative.

For example, the process [A] is intended to be illustrated by the following equation:

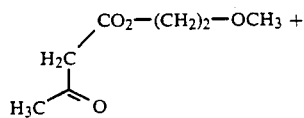

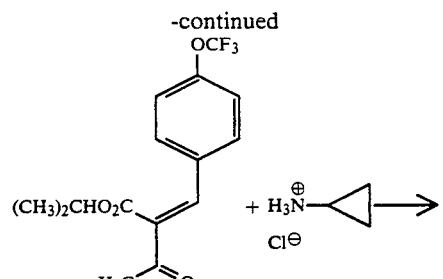

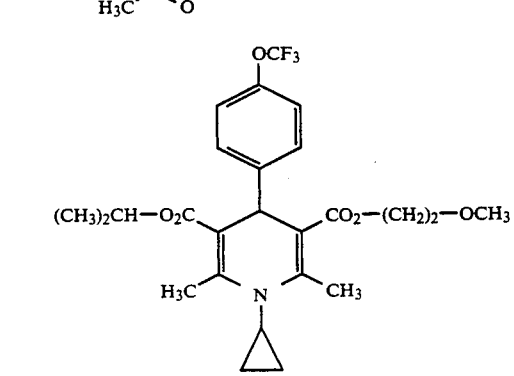

Suitable solvents are water or organic solvents which do not change under the reaction conditions. These preferably include alcohols such as methanol, ethanol, propanol or isopropanol, ethers such as 1,2-dimethoxyethane, diethyl ether, dioxane, tetrahydrofuran, glycol monomethyl ether or glycol dimethyl ether, or amides such as dimethylformamide, dimethylacetamide or hexamethylphosphoric triamide, or glacial acetic acid, dimethyl sulphoxide, acetonitrile or pyridine. Preferred solvents are pyridine and 1,2-dimethoxyethane.

Suitable bases are in general alkali metal hydrides such as potassium hydride or sodium hydride, or alkali metal alkoxides such as sodium methoxide or potassium methoxide, sodium ethoxide or potassium ethoxide or potassium tert-butoxide. Sodium hydride is preferred.

The base is employed in an amount from 1.0 mol to 1.5 mol, preferably from 1.0 mol to 1.3 mol, relative to 1 mol of the dihydropyridine.

The reaction temperatures can be varied within a relatively wide range. In general, the reaction is carried out between +10° C. and +150° C., preferably between +20 C. and +100° C. In particular, it is carried out at the boiling temperature of the respective solvent.

The reaction can be carried out at normal pressure, but also at elevated or reduced pressure. In general, it is carried out at normal pressure.

When carrying out process variants A and B according to the invention, any desired ratio of the substances participating in the reaction can be used. In general, however, the reaction is carried out with molar amounts of the reactants. The substances according to the invention are preferably isolated and purified by distilling off the solvent in vacuo and recrystallising the residue, which may only be obtained in crystalline form after icecooling, from a suitable solvent. In some cases, it may be necessary to purify the compounds according to the invention by chromatography.

The aldehydes of the general formula (II) are known or can be prepared by a customary method [compare German Offenlegungsschrift 2,165,260; 2,401,665; T. D. Harris, G. P. Roth, J. Org. Chem. 44, 2004 (1979); W. J.

Dale, H. E. Hennis, J. Am. Chem. Soc. 78, 2543 (1956); Chem. Abstr. 59, 13929 (1963)].

The compounds of the general formulae (III), (IV), (VIII) and (IX) are known [compare, for example, MSD Book 2, 22506; Beilstein 3,632; 3, 654].

The ylidene compounds of the general formulae (V) and (VI) are known or can be prepared by a customary method [compare Lieb. Ann. Chem. 602, 14 (1957)].

The compounds of the general formula (VII) are known [compare Beil. 4, 87 and 12, 3].

Alkylating agents which can be employed in the process are, for example, alkyl halides, sulphonic acid esters or substituted or unsubstituted dialkyl sulphates, preferably alkyl iodides or p-toluenesulphonic acid esters.

The alkylation is carried out in the abovementioned solvents at temperatures from 0° C. to +150° C., preferably at +20° C. to +100° C. at normal pressure.

In the case of the preparation of the enantiomerically pure esters of the general formula (I) via the corresponding enantiomerically pure acids, suitable activating reagents for the preparation of the reactive acid derivatives before esterification are, in addition to the inorganic halides such as thionyl chloride, phosphorus trichloride or phosphorus pentachloride, carbonyldiimidazole, carbodiimides such as cyclohexylcarbodiimide or 1-cyclohexyl-3-[2-(N-methyl-morpholino)ethyl]carbodiimide p-toluenesulphonate or N-hydroxyphthalimide or N-hydroxy-benzotriazole in the presence of dicyclohexylcarbodiimide.

Suitable solvents for the reactions with the appropriate alcohols are the abovementioned solvents with the exception of the alcohols.

Preferably, the preparation of the enantiomerically pure compounds of the general formula (I) takes place via a chromatographic separation on chiral columns according to a customary method.

The new compounds according to the invention exhibit an unforeseeable, useful spectrum of pharmacological action.

Combined with a neutral blood pressure behaviour in a dose range up to at least 10 mg/kg i.v. and $\leq 100$ mg/kg p.o., as cerebral therapeutics they influence neuronal factors positively.

They can therefore be employed for the preparation of medicaments for the prophylaxis and treatment of disturbances of neuronal function, even those which are based on circulatory disorders. These include the elimination of cognitive deficits, the improvement of learning and memory powers, and the treatment of Alzheimer's disease.

PASSIVE AVOIDANCE TEST

A week before the start of the test, the rats were placed in a noise-impenetrable chamber in which all tests are carried out. During test run 1 (t=0h) each animal was placed on a small black platform which was brightly illuminated by a 60 W light bulb. The platform had an entrance to a dark section having a wire mesh floor. The latency to enter the dark section was measured. After 4 hours, this test was carried out a second time under identical conditions. By this means, the animals were familiarised with the test situation.

During the 3rd experimental run after 24 h, the shock test, the animals were exposed for 2 sec. to a 220 µA electric shock on the paws when entering the dark section.

30 min. before the shock test, either the compounds according to the invention (3 groups each containing 10 animals) or, in the respective control group containing 10 animals, placebo were orally administered (1% methyl cellulose).

25 h after the shock test (4th experimental run, reaction test t=48 h), experimental run 1 was repeated.

For all experimental runs, a maximum latency of 180 sec. was allowed.

The differences in the latency values between the control and experimental groups which occurred in the behavioural tests were statistically evaluated by the Mann-Whitney U tests and a variance analysis.

Differences in the number of animals who have not entered the dark section (maximal avoidance latencies) were statistically assessed using the Fisher exact probability test.

If in the reaction test (4th experimental run) the animals to which the compounds according to the invention had been administered, in contrast to the placebo animals, either needed a longer time to enter the dark section or did not enter this at all, this implies that the animals under the influence of the compounds according to the invention have a better memory of the shock test 23 h previously.

| | Latency values in seconds Example 10 | | | |
|---|---|---|---|---|
| | Test run 1 | Test run 2 | Test run 3 (Shock) | Test run 4 (Retention) |
| Placebo | 14.4(2.23) | 6.9(0.74) | 66(1.34) | 126.4(22.72) |
| 2.5 | 26.8(11.35) | 9.6(1.83) | 7.9(1.99) | 162.4(12.84) |
| 5.0 | 15.6(2.28) | 7.4(1.64) | 6.0(1.15) | 170.9(6.44) |
| 10.0 | 15.6(2.83) | 11.4(4.91) | 3.7(0.62) | 180.0(0.00) |

The present invention includes pharmaceutical preparations which, in addition to non-toxic, inert pharmaceutically suitable excipients, contain the compounds according to the invention, and to processes for the production of these preparations.

Apart from the compounds according to the invention, the abovementioned pharmaceutical preparations may also contain other pharmaceutical active compounds.

The abovementioned pharmaceutical preparations are prepared in a customary manner by known methods, for example by mixing the active compound or compounds with the excipient or excipients.

In general, it has proved advantageous to administer the active compound or compounds according to the invention in total amounts of about 0.5 to about 500, preferably 1 to 100, mg/kg of body weight every 24 hours, if appropriate in the form of several individual doses, to achieve the desired results. An individual dose contains the active compound or compounds preferably in amounts from about 1 to about 80, in particular 1 to 30, mg/kg of body weight. However, it may be necessary to depart from the dosages mentioned, in particular depending on the type and the body weight of the subject to be treated, the nature and the severity of the disease, the type of preparation and the administration of the medicament and the period or interval within which administration takes place.

PREPARATION EXAMPLES

Example 1

Isopropyl 2-methoxyethyl (+)-4-(4-chlorophenyl)-1,2,6-trimethyl-1,4-dihydropyridine-3,5-dicarboxylate

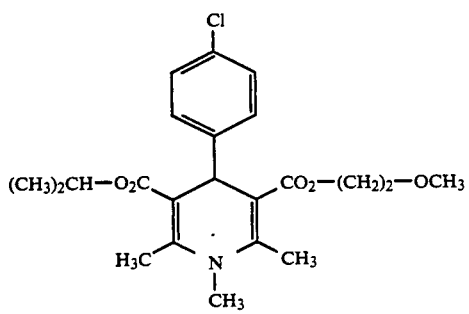

3.5 g (8.6 mmol) of isopropyl 2-methoxyethyl (+)-4-(4-chlorophenyl)-2,6-dimethyl-1,4-dihydropyridine-3,5-dicarboxylate are dissolved 40 ml of 1,2-dimethoxyethane, the solution is treated at 0° C. with 310 mg of sodium hydride (80% strength in white oil, about 10.3 mmol) and the mixture is stirred at this temperature for 30 min. 0.65 ml (10.3 mmol) of iodomethane is then added and the mixture is stirred at 0° C. for 1 h and at room temperature for 20 h. The reaction mixture is rendered weakly acidic with glacial acetic acid and concentrated in vacuo, and the residue is taken up in dichloromethane. After washing with water, drying over sodium sulphate and concentration, the resulting crude product is purified by chromatography on silica gel in the eluent dichloromethane/ethyl acetate 20:1 and 2.6 g (72% of theory) of the title compound are thus obtained.

$[\alpha]_D^{20} + 13.7$ (c=0.907, CHCl$_3$)

In analogy to the procedure of Example 1, the examples shown in Table 1 are prepared:

TABLE 1

| Ex. No. | R$^1$ | Yield (% of theory) | M.p. °C. | $[\alpha]_D^{20}$ |
|---|---|---|---|---|
| 2 | —Cl | 54 | oil | −7.8 (c = 1.08, CHCl$_3$) (−)-enantiomer |
| 3 | —Cl | 64 | oil | racemate |
| 4 | —F | 55 | oil | racemate |
| 5 | —CN | 54 | oil | racemate |
| 6 | —F | 60 | oil | −15.7 (CHCl$_3$) (−)-enantiomer |
| 7 | —F | 63 | oil | +18.9 (CHCl$_3$) (+)-enantiomer |
| 8 | —OCF$_3$ | 50 | oil | −12.7 (−)-enantiomer |
| 9 | —OCF$_3$ | 68 | oil | −11.4 (CHCl$_3$) |

TABLE 1-continued

| Ex. No. | R$^1$ | Yield (% of theory) | M.p. °C. | $[\alpha]_D^{20}$ |
|---|---|---|---|---|
| 10 | —OCF$_3$ | 60 | 45–47 | (+)-enantiomer racemate |

Example 11

Isopropyl 2-methoxyethyl 1-cyclopropyl-2,6-dimethyl-4-(4-trifluoromethoxyphenyl)-1,4-dihydropyridine-3,5-dicarboxylate

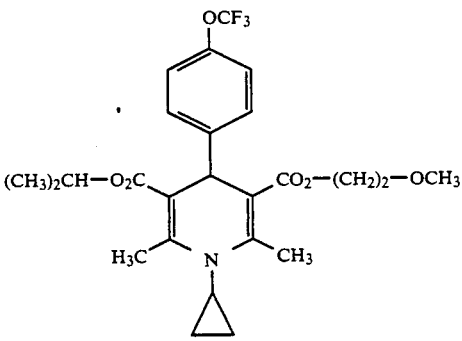

16.4 g (52 mmol) of isopropyl 2-acetyl-4-(4-trifluoromethoxyphenyl)-3-butenoate, 8.3 g (52 mmol) of 2-methoxyethyl acetoacetate and 6.3 g (67 mmol) of cyclopropylamine hydrochloride are heated to reflux in 60 ml of pyridine for 5 h. The residue which remains after concentration of the reaction solution is taken up in dichloromethane, the solution is washed with water, and the organic phase is dried over sodium sulphate and concentrated. Chromatography twice on silica gel in the eluent dichloromethane/ethyl acetate 20:1 and chromatography on silica gel in the eluent petroleum ether/ethyl acetate 3:1 give 2.9 g (11% of theory) of the title compound as an oil.

In analogy to the procedure of Example 11, the examples shown in Table 2 are prepared:

TABLE 2

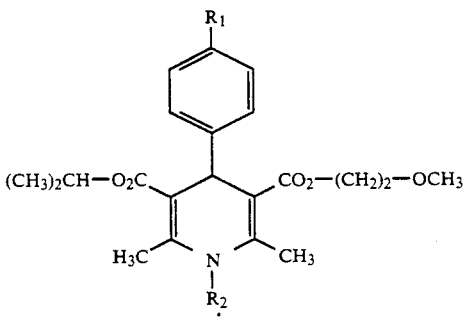

| Ex. No. | R¹ | Yield (% of theory) | M.p. °C. |
|---|---|---|---|
| 12 | —OCF$_3$ | 21 | racemate 49° C. |
| 13 | —CF$_3$ | 12 | racemate oil |

What we claim is:

1. N-Alkylated 1,4-dihydropyridinedicarboxylic acid esters of the general formula

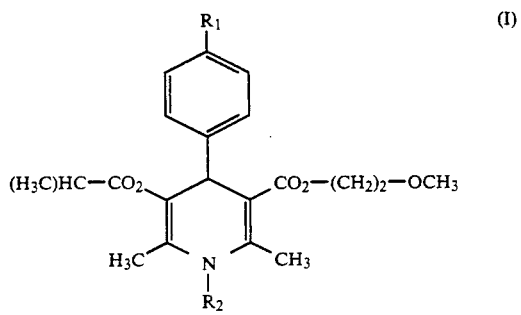

in which
R$^1$ represents trifluoromethoxy, cyano, fluorine, chlorine or trifluoromethyl,
R$^2$ represents methyl, ethyl or cyclopropyl,
with the proviso that R$^1$ must not represent trifluoromethyl if R$^2$ denotes methyl; or a salt thereof.

2. N-Alkylated 1,4-dihydropyridinedicarboxylic acid esters according to claim 1, selected from the group consisting of
   isopropyl 2-methoxyethyl 1,2,6-trimethyl-4-(4-trifluoromethoxyphenyl)-1,4-dihydropyridine-3,5-dicarboxylate,
   isopropyl 2-methoxyethyl 1,2,6-trimethyl-4-(4-cyanophenyl)-1,4-dihydropyridine-3,5-dicarboxylate,
   isopropyl 2-methoxyethyl 1-ethyl-2,6-dimethyl-4-(4-trifluoromethoxyphenyl)-1,4-dihydropyridine-3,5-dicarboxylate,
   isopropyl 2-methoxyethyl 1,2,6-trimethyl-4-(4-chlorophenyl)-1,4-dihydropyridine-3,5-dicarboxylate,
   isopropyl 2-methoxyethyl 1,2,6-trimethyl-4-(4-fluorophenyl)-1,4-dihydropyridine-3,5-dicarboxylate,
   isopropyl 2-methoxyethyl 1-ethyl-2,6-dimethyl-4-(4-trifluoromethylphenyl)-1,4-dihydropyridine-3,5-dicarboxylate, and
   isopropyl 2-methoxyethyl 1-cyclopropyl-2,6-dimethyl-4-(4-trifluoromethoxyphenyl)-1,4-dihydropyridine-3,5-dicarboxylate,
in the form of their racemates (+)- or (−)-isomers.

3. N-Alkylated 1,4-dihydropyridinedicarboxylic acid esters according to claim 1, selected from the group consisting of
   isopropyl 2-methoxyethyl (+)-1,2,6-trimethyl-4-(4-trifluoromethoxyphenyl)-1,4-dihydropyridine-3,5-dicarboxylate,
   isopropyl 2-methoxyethyl (+)-1,2,6-trimethyl-4-(4-trifluoromethoxyphenyl)-1,4-dihydropyridine-3,5-dicarboxylate,
   isopropyl 2-methoxyethyl (−)-1,2,6-trimethyl-4-(4-trifluoromethoxyphenyl)-1,4-dihydropyridine-3,5-dicarboxylate,
   isopropyl 2-methoxyethyl (+)-1,2,6-trimethyl-4-(4-chlorophenyl)-1,4-dihydropyridine-3,5-dicarboxylate,
   isopropyl 2-methoxyethyl (+)-1,2,6-trimethyl-4-(4-chlorophenyl)-1,4-dihydropyridine-3,5-dicarboxylate, and
   isopropyl 2-methoxyethyl (−)-1,2,6-trimethyl-4-(4-chlorophenyl)-1,4-dihydropyridine-3,5-dicarboxylate.

4. An N-alkylated 1,4-dihydropyridinedicarboxylic acid ester of the formula:

(I)

in which
R$_1$ represents trifluoromethyl or trifluoromethoxy; and
R$_2$ represents methyl, ethyl or cyclopropyl;
with the proviso that R$_1$ must not represent trifluoromethyl if R$_2$ represents methyl; or a salt thereof.

5. A compound according to claim 4, wherein such compound is isopropyl 2-methoxyethyl-1,2,6-trimethyl-4-(4-trifluoromethoxyphenyl)-1,4-dihydropyridine-3,5-dicarboxylate or a salt thereof.

6. A compound according to claim 4, wherein such compound is (+)-isopropyl 2-methoxyethyl-1,2,6-trimethyl-4-(4-trifluoromethoxyphenyl)-1,4-dihydropyridine-3,5-dicarboxylate or a salt thereof.

7. A compound according to claim 4, wherein such compound is (−)-isopropyl 2-methoxyethyl-1,2,6-trimethyl-4-(4-trifluoromethoxyphenyl)-1,4-dihydropyridine-3,5-dicarboxylate or a salt thereof.

8. A composition for the treatment and prophylaxis of disturbances of the neuronal function comprising an amount effective therefor of a compound or salt thereof according to claim 1 and a diluent.

9. A method of treating and for the prophylaxis of disturbances of the neuronal function in a patient in need thereof which comprises administering to such patient an amount effective therefor of a compound or salt thereof according to claim 1.

10. A composition for the treatment and prophylaxis of disturbances of neuronal function comprising an amount effective therefor of a compound or salt thereof according to claim 4 and a diluent.

11. A method of treating and for the prophylaxis of disturbances of the neuronal function in a patient in need thereof which comprises administering to such patient an amount effective therefor of a compound or salt thereof according to claim 4.

* * * * *

UNITED STATES PATENT AND TRADEMARK OFFICE
CERTIFICATE OF CORRECTION

PATENT NO. : 5,328,931
DATED : July 12, 1994
INVENTOR(S) : Rosen, et al.

It is certified that error appears in the above-indentified patent and that said Letters Patent is hereby corrected as shown below:

Column 10, line 42, after "dicarboxylate" insert --[racemate]--

Column 10, line 46, after "dicarboxylate" insert --[(+) - enantiomer]--

Signed and Sealed this

Twelfth Day of October, 1999

Attest:

Q. TODD DICKINSON

Attesting Officer

Acting Commissioner of Patents and Trademarks